US011130742B2

(12) United States Patent
Wohl, Jr. et al.

(10) Patent No.: US 11,130,742 B2
(45) Date of Patent: Sep. 28, 2021

(54) ANISOTROPIC COPOLY(IMIDE OXETANE) COATINGS AND ARTICLES OF MANUFACTURE, COPOLY(IMIDE OXETANE)S CONTAINING PENDANT FLUOROCARBON MOIETIES, OLIGOMERS AND PROCESSES THEREFOR

(71) Applicant: United States of America as represented by the Administrator of NASA, Washington, DC (US)

(72) Inventors: Christopher J. Wohl, Jr., Suffolk, VA (US); John W. Connell, Yorktown, VA (US); Emilie J. Siochi, Newport News, VA (US); Joseph G. Smith, Jr., Smithfield, VA (US)

(73) Assignee: United States of America as represented by the Administrator of NASA, Washington, DC (US)

( * ) Notice: Subject to any disclaimer, the term of this patent is extended or adjusted under 35 U.S.C. 154(b) by 0 days.

(21) Appl. No.: 16/854,265

(22) Filed: Apr. 21, 2020

(65) Prior Publication Data

US 2020/0247770 A1      Aug. 6, 2020

Related U.S. Application Data

(62) Division of application No. 15/819,916, filed on Nov. 21, 2017, now Pat. No. 10,626,098, which is a division of application No. 13/286,715, filed on Nov. 1, 2011, now Pat. No. 9,822,088.

(60) Provisional application No. 61/469,204, filed on Mar. 30, 2011.

(51) Int. Cl.
| | |
|---|---|
| *C07D 305/08* | (2006.01) |
| *C09D 179/08* | (2006.01) |
| *C08G 73/10* | (2006.01) |
| *C08G 65/18* | (2006.01) |
| *C08G 65/322* | (2006.01) |
| *C08G 65/333* | (2006.01) |
| *C08G 65/16* | (2006.01) |
| *C08G 73/02* | (2006.01) |
| *C08L 67/00* | (2006.01) |
| *C08G 63/68* | (2006.01) |

(52) U.S. Cl.
CPC .......... *C07D 305/08* (2013.01); *C08G 65/16* (2013.01); *C08G 65/18* (2013.01); *C08G 65/322* (2013.01); *C08G 65/33389* (2013.01); *C08G 73/02* (2013.01); *C08G 73/105* (2013.01); *C08G 73/1042* (2013.01); *C09D 179/08* (2013.01); *C08G 63/68* (2013.01); *C08L 67/00* (2013.01)

(58) Field of Classification Search
CPC .. C08G 63/68; C08G 63/682; C08G 65/0065; C08G 65/18; C08G 65/226; C08G 73/00; C08G 73/02; C08G 73/16; C08L 67/00; C09D 167/00
See application file for complete search history.

(56) References Cited

U.S. PATENT DOCUMENTS

| | | | |
|---|---|---|---|
| 4,080,319 A * | 3/1978 | Caporiccio | C08G 73/1039 528/183 |
| 4,085,137 A | 4/1978 | Mitsch | |
| 4,760,112 A | 7/1988 | McCready et al. | |
| 4,902,768 A * | 2/1990 | Gerkin | C08G 18/3228 528/68 |
| 4,908,409 A | 3/1990 | Okawa et al. | |
| 5,252,168 A | 10/1993 | Johnston et al. | |
| 5,308,737 A | 5/1994 | Bills et al. | |
| 5,313,000 A | 5/1994 | Stewart | |
| 5,468,841 A | 11/1995 | Malik et al. | |
| 5,637,772 A | 6/1997 | Malik et al. | |
| 6,686,051 B1 | 2/2004 | Weinert et al. | |
| 6,855,775 B2 | 2/2005 | Medsker et al. | |
| 6,872,266 B1 | 3/2005 | Ciaramitaro | |
| 6,972,317 B2 | 12/2005 | Weinert et al. | |
| 7,022,801 B2 | 4/2006 | Medsker | |
| 7,320,829 B2 | 1/2008 | Wright et al. | |
| 7,396,590 B2 | 7/2008 | Wynne | |
| 7,498,375 B2 | 3/2009 | Harashina et al. | |
| 7,585,611 B2 | 9/2009 | Kato et al. | |
| 7,771,793 B2 | 8/2010 | Wynne et al. | |

(Continued)

OTHER PUBLICATIONS

OMNOVA Solutions, Inc., "PolyFox Reactive Polymer Intermediates", Chester, SC.

(Continued)

*Primary Examiner* — Jane L Stanley
(74) *Attorney, Agent, or Firm* — Jennifer L. Riley; Robin W. Edwards; Helen M. Galus

(57) ABSTRACT

Copoly(imide oxetane) materials are disclosed that can exhibit a low surface energy while possessing the mechanical, thermal, chemical and optical properties associated with polyimides. The copoly(imide oxetane)s are prepared using a minor amount of fluorinated oxetane-derived oligomer with sufficient fluorine-containing segments of the copoly (imide oxetane)s migrate to the exterior surface of the polymeric material to yield low surface energies. Thus the coatings and articles of manufacture made with the copoly (imide oxetane)s of this invention are characterized as having an anisotropic fluorine composition. The low surface energies can be achieved with very low content of fluorinated oxetane-derived oligomer. The copolymers of this invention can enhance the viability of polyimides for many applications and may be acceptable where homopolyimide materials have been unacceptable.

17 Claims, No Drawings

(56) References Cited

U.S. PATENT DOCUMENTS

| | | | |
|---|---|---|---|
| 7,928,153 B2 | 4/2011 | Dershem | |
| 9,822,088 B2 * | 11/2017 | Wohl | C08G 65/33389 |
| 10,626,098 B2 * | 4/2020 | Wohl, Jr. | C08G 73/105 |
| 2004/0224164 A1 * | 11/2004 | Wright | C08L 67/00 |
| | | | 428/421 |
| 2010/0084171 A1 * | 4/2010 | Fujihara | C08G 73/1007 |
| | | | 174/258 |
| 2010/0173085 A1 * | 7/2010 | Jariwala | C08L 79/00 |
| | | | 427/385.5 |

OTHER PUBLICATIONS

OMNOVA Solutions, Inc., "PolyFox Structures", Chester, SC.

Yong-Kuk Yun, Doo-Hyun Ko, Jung-Il Jin, Yoon Soc Kang, Wang-Cheol Zin, and Byung-Wook Jo, "Synthesis and Characterization of New Chiral Side Chain Liquid Crystalline Polyoxetanes", American Chemical Society, Macromolecules 2000, 33, pp. 6653-6663.

Richard Thomas, "Fluorinated Oxetane Oligomers as Versatile Intermediates for Polymer Modification", Paint and Coatings Industry, Mar. 1, 2008.

Christopher J. Wohl et al., "Copolymide Surface Modifying Agents for Particle Adhesion Mitigation" NASA™ 20110015414, Aug. 28, 2011, 2 pages.

* cited by examiner

ANISOTROPIC COPOLY(IMIDE OXETANE) COATINGS AND ARTICLES OF MANUFACTURE, COPOLY(IMIDE OXETANE)S CONTAINING PENDANT FLUOROCARBON MOIETIES, OLIGOMERS AND PROCESSES THEREFOR

CROSS-REFERENCE TO RELATED APPLICATION

This patent application is a divisional of and the claims the benefit of priority to U.S. Non-Provisional patent application Ser. No. 15/819,916, filed Nov. 21, 2017, which is a divisional of and claims the benefit of and priority to U.S. Non-Provisional patent application Ser. No. 13/286,715, filed Nov. 1, 2011, which claims the benefit of and priority to U.S. Provisional Application No. 61/469,204, filed Mar. 30, 2011, each of the foregoing applications is hereby incorporated by reference in its entirety.

STATEMENT REGARDING FEDERALLY SPONSORED RESEARCH AND DEVELOPMENT

This invention was made in part with Government support. The Government may have certain rights in this invention.

FIELD OF THE INVENTION

This invention pertains to copoly(imide oxetane)s having low adhesion surface properties and to oligomers useful to make such copoly(imide oxetane)s. The oxetane oligomers contain fluorocarbon moieties that enable the copoly(imide oxetane)s to achieve the low adhesion surface properties with relatively low oxetane content. The invention also pertains to processes for making the copoly(imide oxetane)s and anisotropic coatings and articles of manufacture from them.

BACKGROUND TO THE INVENTION

Marine biofouling, membrane fouling, insect adhesion on aircraft surfaces, microbial contamination of sterile environments, and surface particle contamination all present unique challenges. An array of mitigations strategies has been pursued to address these problems.

Passive strategies for minimizing fouling or contamination of surfaces are beneficial especially in environments where active mitigation of the fouling or contamination is impractical or impossible. For instance, lunar dust compromised seals, clogged filters, abraded visors and space suit surfaces, and was a significant health concern during the Apollo missions. Accordingly, passive mitigation utilizing materials with an intrinsic resistance to surface contamination would be advantageous for such applications. One passive mitigation strategy is modification of a material's surface energy either chemically or topographically or both.

Any surface material needs to meet the requirements of its application. High performance polymeric materials have been developed to address various requirements for mechanical, thermal, and optical properties. Modification of the chemical constituency of these polymeric materials can alter their properties. Thus, modification of high performance polymeric materials is often hampered due to degradation of the desired characteristic properties. Modifying a polymeric material to influence surface characteristics is problematic as addition of sufficient modifier to the bulk chemical composition to achieve the desired surface modification could also result in the diminution of other important performance properties of the polymeric material. If the modifier is well dispersed within the polymer matrix, a majority of the modifier will be located in the interior of the polymeric structure where it will not contribute to the structure's surface properties. This is especially problematic if the modifier is expensive, provides no other performance enhancement or diminishes bulk properties of the polymeric material.

Polymeric materials with low adhesion surface properties have been demonstrated to be effective in a wide variety of applications. Low surface energy polymeric materials, i.e., those exhibiting a high water contact angle, have been used to reduce marine biofouling, water and ice adhesion, and biofilm formation; to improve oxidation, corrosion and stain resistance; to minimize dust adhesion; and to modify the performance of microfluidic systems and biomedical devices. The ability to selectively modify the surface energy of high performance polymeric materials without sacrificing their superior mechanical, thermal and optical properties is of significant utility.

A number of approaches have been suggested to yield polymeric materials with low surface energy. One of the most well known polymeric materials having low surface energy are fluorinated, aliphatic polymers such as those available under the trade name TEFLON® fluoropolymers. The presence of both aliphatic carbon species and fluorine atoms contributes to the low surface energy of this class of materials. These polymeric materials have an approximate homogeneous composition, do not use a controlled modification, and thus cannot be tailored for the introduction of further surface features. Moreover, they do not adhere well to substrates and are difficult to process. Generally the polymer is provided as a powder to be coated and sintered onto the substrate. Another approach is to vapor deposit highly fluorinated carbonaceous materials to various substrates.

Another approach to provide low surface energy polymeric materials is to incorporate surface modifying agents into the materials. These surface modifying agents are thermodynamically driven to migrate to the surface of the polymeric material preferentially due to more favorable interactions at the air interface compared to the polymeric matrix.

Omnova Solutions Inc. offers a family of hydroxyl terminated oxetane-derived oligomers under the trade name POLYFOX® fluorochemicals and have found commercial application in polymeric systems. Fluorine-containing oxetane derivatives have been used extensively as surface modification agents for modification of urethanes. See, for instance, Malik, et al., United States patent application publication No. US 2004/0087759. Medsker, in U.S. Pat. No. 7,022,801 and Thomas, et al., in United States patent application publication No. 2003/0092862, disclose the use of fluoro-containing oxetane polymers to impart wetting, flow or leveling properties to a variety of coatings while producing little foam.

Wynne, U.S. Pat. No. 7,396,590 and Wynne, et al., in U.S. Pat. No. 7,771,793 disclose making polymeric articles or coatings that have a surface phase having an activity of interest. They disclose preparing a surface active telechelic that includes both a surface active segmer which favors migration to the surface of a bulk polymer and one or more functional segmers which provide an activity of interest (e.g., biocide, bioactive, UV protective, hydrophobic, hydrophylic, etc.). The telechelics disclosed include those made using fluorine-containing oxetanes.

Weinert, et al, in U.S. Pat. No. 6,972,317 disclose monofunctional polyfluorooxetane oligomers and polymers that can be reacted with cyclic ethers or functionalized with a functional end group such as an acrylate, a methacrylate, an allylic, an amine, etc., for use in radiation curable or thermal curable coating compositions. They believe that the fluorinated side groups of the fluorooxetanes are disproportionately present at the interfaces between the coating and substrate and between the coating and the atmosphere.

Polyimides are known for their thermal stability, fire resistance, good chemical resistance and excellent mechanical properties. Polyimides have good mechanical elongation and tensile strength and good adherence properties to many substrates. Some polyimides exhibit high optical clarity. Polyimides have found application as coatings, insulating films in the electronic industry, fibers and articles of manufacture including for demanding applications such as bushings, bearings in jet engines, or other constructive parts.

Accordingly, a need exists for a low surface energy polymeric material that has the mechanical, thermal, chemical and optical properties associated with polyimides.

SUMMARY

In accordance with this invention copoly(imide oxetane) materials are provided that can possess the mechanical, thermal, chemical and optical properties associated with polyimides and exhibit a low energy surface. By this invention, copoly(imide oxetane)s are prepared using a minor amount of an amino terminated fluorinated oxetane-derived oligomer. Sufficient fluorine-containing segments of the copoly(imide oxetane)s migrate to the exterior surface of the polymeric material to afford low surface energies. In preferred copoly(imide oxetane) coatings and articles of manufacture, the surface is saturated with fluoro-groups even at very low, e.g., below about 0.5 mass percent oxetane oligomer in the copoly(imide oxetane). Although greater amounts of oxetane oligomer could be used, often virtually no further improvement in surface hydrophobicity is observed. Hence it is possible with the copoly(imide oxetane)s of this invention to tailor the surface properties while still maintaining the physical properties of the polyimide. The copoly(imide oxetane)s of this invention can enhance the viability of polyimides for many applications and may be acceptable where homopolyimide materials have been unacceptable.

In the way of an overview, the copoly(imide oxetane)s of this invention are characterized as containing divalent radicals of an oligomer derived from a fluorine-containing oxetane, preferably oxetanes containing a perfluorinated carbon on a substituent on the beta carbon of the oxetane. The oxetane oligomer content of the copolymer is often less than about 10 or 15, preferably less than about 1, mass percent of the copolymer. In the some preferred aspects, the oxetane oligomer content of the copolymer is between 0.001 and 0.1, mass percent of the copolymer. Often the water contact angle is greater than about 85°, preferably greater than about 90°. If desired, concentrations higher than 15 mass percent oxetane oligomer may be used to make the copoly(imide oxetane). Although at these high levels of oxetane content, physical properties of the copolymer such as glass transition temperature, tensile strength and abrasion resistance will be inferior to the corresponding polyimide; however, the copoly(amic acid oxetane) and copoly(imide oxetane) will have low surface energy and in some instances, the copolymer may be soluble in polar organic solvents such as dimethylacetamide, acetone, and tetrahydrofuran or combinations thereof.

One aspect of the invention pertains to oligomers represented by the formula:

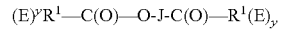

wherein:

J is $[CH_2-CR^2R^3-CH_2-O]_m$ or
$[(CH_2-CR^2R^3-CH_2-O)_p-(R^6-O)_q-(CH_2-CR^2R^3-CH_2-O)_r-]$ wherein $R^6$ is a substituted or unsubstituted aliphatic or aromatic moiety of 2 to 16 carbons, preferably $CR^7CH_2-$ wherein $R^7$ is H or methyl;

E is $-NO_2$ or $-NH_2$, and preferably each E is either $-NO_2$ or $-NH_2$;

y is 1 or 2, and preferably each y is 1;

$R^1$ is an aliphatic or aromatic hydrocarbon moiety of 1 to 10 carbon atoms, preferably $R^1$ is a divalent phenyl group;

$R^2$ is $-H$, $-F$, or alkyl of 1 to 6 carbon atoms, and preferably is an alkyl of 1 to 3 carbon atoms, and most often methyl;

$R^3$ is $-F$, $-R^4H_{(n-a)}F_a$, $-R^5-O-R^4H_{(n-a)}F_a$, or $-O-R^4H_{(n-a)}F_a$, wherein $R^4$ is an alkyl or ether moiety of 1 to 30 carbons, $R^5$ is an alkyl moiety of 1 to 30 carbons, a is an integer of 3 to n, and n is twice the number of carbon atoms in the alkyl moiety plus 1; and m is between about 4 and 500, preferably between about 6 and 100, p is between about 4 and 150, q is between about 1 and 150, preferably between about 4 and 150.

Preferably the omega carbon of $R^4$ has three fluoride substituents. Preferably, $R^5$ is $-CH_2-O-C(R')_2-CF_3$, wherein R' is $-H$ or $-F$.

Preferred oligomers of this invention are represented by the formula:

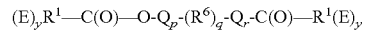

wherein:

E, y, $R^6$, p, q, r and $R^1$ are as defined above; and

Q is derived from the oligomerization of oxetane monomer wherein at least 40 mole percent of the oxetane monomer is substituted at the beta carbon with at least one substituent containing at least one perfluorinated carbon atom.

The substituted oxetane monomer from which Q is derived can be represented by the formula:

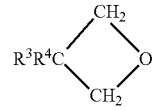

wherein:

$R^3$ is $-F$, $-R^4H_{(n-a)}F_a$, $-R^5-O-R^4H_{(n-a)}F_a$, and $-O-R^4H_{(n-a)}F_a$, wherein $R^4$ is an alkyl or ether moiety of 1 to 30 carbons, and preferably is an alkyl of 1 to 3 carbon atoms, and most often methyl, $R^5$ is an alkyl moiety of 1 to 30 carbons, a is an integer of 3 to n, and n is twice the number of carbon atoms in the alkyl moiety plus 1.

Another aspect of this invention pertains to polyamic acids that can be imidized to make copoly(imide oxetane)s having the structure represented by:

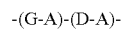

wherein:
G is represented by the formula

—NH—R¹—C(O)—O-J-C(O)—R¹—HN— wherein:
R¹ and J are as defined above;
A is represented by the formula

——[C(O)    C(O)]——
       > L <
    HOC(O)   (O)COH wherein:
L is a hydrocarbyl-containing moiety of 2 to 100 carbon atoms optionally containing divalent radicals selected from the group consisting of oxygen, silyl, sulfur, carbonyl, sulfonyl, phosphonyl, perfluoro, tertiary amino, and imido;
D is represented by the formula

—NH—Z—NH— wherein:
Z is a hydrocarbyl-containing moiety of 1 to 100 carbon atoms optionally containing divalent radicals selected from the group consisting of oxygen, sulfur, silyl, carbonyl, sulfonyl, phosphonyl, perfluoro, tertiary amino, and imido.

Another aspect of this invention pertains to copoly(imide oxetane)s containing the oxetane oligomers of this invention. The copoly(imide oxetane)s are prepared by using the oxetane oligomers of this invention wherein E is —NH₂, and generally the copoly(imide oxetane) contains less than about 10, say, 0.001 to 5, preferably, 0.001 to 0.1, mass percent of the oxetane oligomer. The copoly(imide oxetane)s of this invention can be represented by the structure:

-(G-M)-(D-M)- wherein:
G is represented by the formula

=N—R¹—C(O)—O-J-C(O)—R¹—N= wherein:
R¹, and J are defined above;
M is represented by the formula (—C(O))₂-M-(C(O)—)₂ wherein:
L is as defined above;
D is represented by the formula

=N—Z—N= wherein:
Z is defined as above.

The copoly(imide oxetane) may be a block co-polymer or a random co-polymer.

A yet further aspect of this invention pertains to coatings having an outer surface and a bonding surface that comprise the copoly(imide oxetane)s of this invention. The coatings are characterized as having an anisotropic distribution of fluorine atoms over its thickness with a higher concentration at the outer surface. Preferred coatings have a water contact angle of at least 90° at the outer surface. The coating may be on any suitable surface including metal, ceramic, glass, wood, paper, fibers, textiles, membranes, or polymer surfaces. The coatings can be prepared by applying on a substrate a solution containing a copoly(amic acid oxetane) of this invention in a volatile solvent for the copoly(amic acid oxetane) to form a copoly(amic acid oxetane)-containing coating, and then subjecting the copoly(amic acid oxetane)-containing coating to drying and imidization conditions to form the anisotropic copoly(imide oxetane)-containing coating. In some aspects, the copoly(imide oxetane) of this invention may be soluble in a low boiling solvent in an imide form, thus allowing for it to be cast directly on an article and then solvent evaporated to form the coating.

Another aspect of this invention pertains to articles of manufacture having an outer surface on a polymeric matrix comprising the copoly(imide oxetane) of this invention wherein the article of manufacture has a higher concentration of fluorine atoms at its outer surface than that used to make the polymeric matrix. The article may be made by casting, molding, extruding or other suitable process. For example, the article of manufacture may be made by forming a polymeric matrix containing the copoly(amic acid oxetane) of this invention into the shape of the article of manufacture and subjecting the article of manufacture to imidization conditions to form the article of manufacture. The polymeric matrix may be in a slurry or solvent when formed into the sought shape or may be in the form of a substantially dry particulate, e.g., having a major dimension of between about 20 and 2000 microns. The particulate polymeric matrix may be formed into the sought shape under pressure and subjected to imidization conditions to form the copoly(imide oxetane)-containing article of manufacture.

An aspect of this invention pertains to making coatings and articles of manufacture by contacting a polyamic acid coating or article of manufacture with a diamine oligomer of this invention or a copoly(amic acid oxetane) of this invention at its exterior surface and then subjecting the coating or article of manufacture to imidization conditions. The polyamic acid coating or article of manufacture need not contain fluorine, yet upon imidization, the fluorine-containing oxetane oligomer or copoly(imide oxetane) becomes integral with the material of the coating or article of manufacture without gross phase segregation.

An additional aspect of the invention pertains to processes for making copoly(amic acid oxetane)s and copoly(imide oxetane)s comprising:

a. reacting an oxetane oligomer of the formula

H—O-J-H wherein J is as defined above, with an acyl reagent of the formula O₂N—R¹C(O)X, wherein R¹ is aliphatic or aromatic hydrocarbon moiety of 1 to 10 carbon atoms and X is selected from the group consisting of bromide, chloride and iodide, —H, —OH, and —OR⁸, wherein R⁸ is alkyl of 1 to 3 carbon atoms, under nucleophilic reaction conditions, to provide nitro-terminated oligomer;

b. hydrogenating the nitro-terminated oligomer under hydrogenation conditions including the presence of hydrogenation catalyst to convert nitro moieties to amine moieties and provide diamine-terminated oligomer;

c. reacting the diamine-terminated oligomer with at least one of
(i) dianhydride of the formula

O(C(O))₂-L-(C(O))₂O            (I)

wherein L is as defined above; preferably in the presence of one or more diamines of the formula

—NH—Z—NH— (II)

wherein: Z is as defined above, and (ii) anhydride-terminated prepolymer of (I) and (II) preferably having a weight average molecular weight of between about 1000 and 500,000 g/mol, under condensation polymerization conditions, to provide the polyamic acid; and d. subjecting the polyamic acid to imidization conditions, preferably either a thermal ring closure including a temperature of at least about 120° C., say, between 150° C. to 400° C., to provide the polyimide, or a chemical ring closure in the presence of dehydrating and ring-closing catalyst such as one or more of pyridine, triethylamine, acetic anhydride or the like at a temperature in the range of about −20° C. to 200° C.

A yet further aspect of this invention comprises a polymer composite, which may be in the form of a coating or article of manufacture, said composite comprising copolymer containing fluoro-containing oxetane oligomer and a particulate filler to provide a water contact angle of at least 100°. Examples of copolymers include, but are not limited to, block and random copolymers such as polyester/polyoxetane copolymers such as from ethylene terephthalate, propylene terephthalate, trimethylene terephthalate and butylene terephthalate; acrylic copolymers such as copoly(acrylate oxetane), copoly(methacrylate oxetane); copoly(urethane oxetane); copoly(amide oxetane) such as from butyrolactam, caprolactam, lauryl lactam, and polyamides from the reaction of adipic acid or sebacic acid with a diamine such as hexamethylene diamine; copoly(imide oxetane); copoly(siloxane oxetane); copoly(urea oxetane); copoly(ether oxetane) such as copolymers with polyether ether ketone; copoly(sulfone oxetane); and copoly(sulfide oxetane). The preferred copoly(imide oxetane)s are those of this invention. The particulate fillers may be composed of metal, metal oxides and metal sulfides. Preferably the particulate fillers have a major dimension of less than about 5 microns, more preferably less than about 0.5 micron, and sometimes less than about 0.05 micron. Examples of particulate fillers include, but are not limited to, oxides such as silica, alumina, titania, yttria, zirconia, molybdenum oxide, iron oxide, metals and metal alloys such as gold, silver, copper, germanium, platinum, iron and cobalt/platinum; semiconductors such a lead sulfide, cadmium sulfide, CdSe, CdTe; sulfides such as molybdenum sulfide and cesium sulfide; phosphates such as aluminum phosphate; clays such as montmorillonite, vermiculite, hectorite; carbonates such as calcium carbonate; carbon black, finely ground rubber, and molecular sieves. The amount of filler can vary depending upon particle size and inherent surface energy. In general, the composites contain from about 0.1 to 40, say, 0.5 to 20, mass percent particulate filler based upon the mass of the composite. In preferred aspects of this invention, the composite possesses a water contact angle of at least about 120°.

DETAILED DISCUSSION

Definitions and Procedures

Water contact angle as used herein is the angle that deionized water contacts the surface of the polymer. A FTA 1000B contact angle goniometer available from First Ten Angstroms, Inc., Portsmouth, Va., United States can be used to measure the water contact angle using an 8 milliliter drop.

Polyimides

Polyimides are typically prepared by the reaction between a diamine and a dianhydride under condensation polymerization conditions although it is possible to prepare polyimides by other reactions such as that of a dianhydride and a diisocyanate or a diester of the dianhydride with a diamine. The copoly(imide oxetane)s of this invention use as all or a portion of the diamine component a diamine which is a derivative of a fluorine-containing oxetane oligomer, herein called a FOX diamine.

The FOX diamine preferably constitutes a minor portion by mass of the diamine components used in the synthesis, often less than about 20, preferably less than about 10, and most times between about 0.02 to 0.5, mass percent of the total diamine where the properties of the polyimide are sought. Generally, the amount of FOX diamine is sufficient to provide a water contact angle of at least 85°, preferably at least 90°.

The FOX diamine can be represented by the structure:

—N—R¹—C(O)—O-J-C(O)—R¹—N— as discussed above. One or more FOX diamines can be contained in the copoly(imide oxetane)s of this invention.

The optional diamine may be one or more aliphatic or aromatic diamines and includes diamines containing other hetero atoms. One or more other diamines may be used. Examples of diamines include aliphatic diamines such as trimethylenediamine, tetramethylenediamine, pentamethylenediamine, hexamethylenediamine, 2,2,4-trimethylhexamethylenediamine, 2,4,4-trimethylhexamethylenediamine, octamethylenediamine and nonamethylenediamine; and an alicyclic diamine such as bis(4-aminocyclohexyl)methane and bis(4-amino-3-methylcyclohexyl)methane; aromatic diamines, for example, phenylenediamine, diaminotoluene, 2,4-diaminomesitylene, 3,5-diethyl-2,6-diaminotoluene, xylylenediamine (in particular, metaxylylenediamine, paraxylylenediamine), bis(2-aminoethyl)benzene, biphenylenediamine, a diamine having a biphenyl backbone (e.g., 4,4'-diamino-3,3'-ethylbiphenyl), adiamine having adiphenyl alkane backbone [e.g., diaminodiphenylmethane, bis(4-amino-3-ethylphenyl)methane, bis(4-amino-3-methylphenyl)methane, 3,3'-dichloro-4,4'-diaminodiphenylmethane, 2,2'-bis(4-aminophenyl)propane], bis(4-aminophenyl)ketone, bis(4-aminophenyl)sulfone, or 1,4-naphthalenediamine, and an N-substituted aromatic diamine thereof; alicyclic diamine such as 1,3-cyclopentanediamine, 1,4-cyclohexanediamine, and bis(4-amino-3-methylcyclohexyl)methane; an aliphatic amine, such as trimethylenediamine, tetramethylenediamine, pentamethylenediamine, hexamethylenediamine, 2,2,4-trimethylhexamethylenediamine, 2,4,4-trimethylhexamethylenediamine, and octamethylenediamine, and an N-substituted aliphatic diamine thereof; and ether diamines such as poly(alkylene ether)diamines including poly(ethylene ether)diamine, poly(propylene ether)diamine, poly(tetramethylene ether)diamine; random or block copolymers of ethylene oxide and propylene oxide including propylene oxide and poly(propylene oxide) terminated poly(ethylene ether)diamine, 4,4'-oxydianiline; and aminated random or block copolymers of tetrahydrofuran with minor amounts of a second monomer such as ethylene oxide, propylene oxide, methyl tetrahydrofuran, bis[4-(3-aminophenoxy)phenyl]methane, bis[4-(4-aminophenoxy)phenyl]methane, 1,1-bis[4-(3-aminophenoxy)phenyl]ethane, 1,1-bis[4-(4-aminophenoxy)phenyl]ethane, 1,2-bis[4-(3-aminophenoxy)phenyl]ethane, 1,2-bis[4-(4-aminophenoxy)phenyl]ethane, 2,2-bis[4-(3-aminophenoxy)phenyl]propane, 2,2-bis[4-(4-aminophenoxy)phenyl]propane, 2,2-bis[4-(3- aminophenoxy)phenyl]butane, 2,2-bis[4-(4-aminophenoxy) phenyl]butane, 2,2-bis[4-(3-aminophenoxy)phenyl]-1,1,1,3, 3,3-hexafluoropropane, 2,2-bis[4-(4-aminophenoxy) phenyl]-1,1,1,3,3,3-hexafluoropropane, 4,4'-bis(3-aminophenoxy)biphenyl, 4,4'-bis(4-aminophenoxy) biphenyl, bis[4-(3-aminophenoxy)phenyl] ketone, bis[4-(4-aminophenoxy)phenyl] ketone, bis[4-(3-aminophenoxy) phenyl] sulfide, bis[4-(4-aminophenoxy)phenyl] sulfide, bis [4-(3-aminophenoxy)phenyl] sulfone and bis[4-(4-aminophenoxy)phenyl] sulfone.

Any suitable dianhydride or dianhydride combination can be used to make the copoly(imide oxetane) and one or more dianhydrides can be used. Aliphatic and aromatic dianhydrides can find application in making the copoly(imide oxetane)s of this invention. Examples of useful dianhydrides of the present invention include pyromellitic dianhydride (PMDA); 3,3',4,4'-biphenyl tetracarboxylic dianhydride (BPDA); 3,3',4,4'-benzophenone tetracarboxylic dianhydride (BTDA); 4,4'-oxydiphthalic anhydride (ODPA); 3,3', 4,4'-diphenylsulfone tetracarboxylic dianhydride (DSDA); 4,4'-(4,4'-isopropylidenediphenoxy)bis(phthalic anhydride) (BPADA); 2,3,6,7-naphthalene tetracarboxylic dianhydride; 1,2,5,6-naphthalene tetracarboxylic dianhydride; 1,4,5,8-naphthalene tetracarboxylic dianhydride; 2,6-dichloronaphthalene-1,4,5,8-tetracarboxylic dianhydride; 2,7-dichloronaphthalene-1,4,5,8-tetracarboxylic dianhydride; 2,3,3',4'-biphenyl tetracarboxylic dianhydride; 2,2',3,3'-biphenyl tetracarboxylic dianhydride; 2,3,3',4'-benzophenone tetracarboxylic dianhydride; 2,2',3,3'-benzophenone tetracarboxylic dianhydride; 2,2-bis(3,4-dicarboxyphenyl)propane dianhydride; 1,1-bis(2,3-dicarboxyphenyl)ethane dianhydride; 1,1-bis(3,4-dicarboxyphenyl)ethane dianhydride; bis (2,3-dicarboxyphenyl)methane dianhydride; bis(3,4-dicarboxyphenyl)methane dianhydride; 4,4'-(hexafluoroisopropylidene)diphthalic anhydride (6FDA); bis(3,4-dicarboxyphenyl)sulfoxide dianhydride; tetrahydrofuran-2,3,4,5-tetracarboxylic dianhydride; pyrazine-2,3,5,6-tetracarboxylic dianhydride; thiophene-2,3,4,5-tetracarboxylic dianhydride; phenanthrene-1,8,9,10-tetracarboxylic dianhydride; perylene-3,4,9,10-tetracarboxylic dianhydride; bis-1,3-isobenzofurandione; bis(3,4-dicarboxyphenyl)thioether dianhydride; bicyclo[2.2.2]oct-7-ene-2,3,5,6-tetracarboxylicdianhydride; 2-(3',4'-dicarboxyphenyl)5,6-dicarboxybenzimidazole dianhydride; 2-(3',4'-dicarboxyphenyl) 5,6-dicarboxybenzoxazole dianhydride; 2-(3',4'-dicarboxyphenyl)5,6-dicarboxybenzothiazole dianhydride; bis(3,4-dicarboxyphenyl)2,5-oxadiazole 1,3,4-dianhydride; 2,5-(3',4'-dicarboxydiphenylether) 1,3,4-oxadiazole dianhydride; butane-1,2,3,4-tetracarboxylic dianhydride; pentane-1,2,4,5-tetracarboxylic dianhydride; cyclobutane tetracarboxylic dianhydride; cyclopentane-1,2,3,4-tetracarboxylic dianhydride; cyclohexane-1,2,4,5 tetracarboxylic dianhydride; cyclohexane-2,3,5,6-tetracarboxylic dianhydride; 3-ethyl cyclohexane-3-(1,2)5,6-tetracarboxylic dianhydride; 1-methyl-3-ethyl cyclohexane-3-(1,2)5,6-tetracarboxylic dianhydride; 1-ethyl cyclohexane-1-(1,2),3,4-tetracarboxylic dianhydride; 1-propylcyclohexane-1-(2,3),3,4-tetracarboxylic dianhydride; 1,3-dipropylcyclohexane-1-(2,3),3-(2, 3)-tetracarboxylic dianhydride; dicyclohexyl-3,4,3',4'-tetracarboxylic dianhydride; 4,4'-bisphenol A dianhydride; 1,2,3,4-cyclobutanetetracarboxylic acid dianhydride; bicyclo[2.2.2]oct-7-ene-2,3,5,6-tetracarboxylicdianhydride; hydroquinonediphthalic anhydride; ethyleneglycol bis(trimellitic anhydride); 9,9-bis-(trifluoromethyl)xanthenetetracarboxylic dianhydride (6FCDA); 9-phenyl-9-(trifluoromethyl)xanthenetetracarboxylic dianhydride (3FCDA); 9,9-diphenyl-2,3,6,7-xanthenetetracarboxylic dianhydride (PPXDA); 9,9-diphenyl-2,3,6,7-tetramethylxanthene (TMPPX); 9,9-diphenyl-2,3,6,7-xanthenetetracarboxylic bis (p-anisidylimide); 9,9-diphenyl-2,3,6,7-xanthenetetracarboxylic bis(butylimide); 9,9-diphenyl-2,3,6,7-xanthenetetracarboxylic bis(p-tolylimide); 9-phenyl-9-methyl-2,3,6,7-xanthenetetracarboxylic dianhydride (MPXDA); 9-phenyl-9-methyl-2,3,6,7-xanthenetetracarboxylic bis(propylimide); 9-phenyl-9-methyl-2,3,6,7-xanthenetetracarboxylic bis(p-tolylimide); 9,9-dimethyl-2,3,6,7-xanthenetetracarboxylic dianhydride (MMXDA); 9,9-dimethyl-2,3,6,7-xanthenetetracarboxylic bis(propylimide); 9,9-dimethyl-2,3,6,7-xanthenetetracarboxylic bis(tolylimide); 9-ethyl-9-methyl-2,3, 6,7-xanthenetetracarboxlylic dianhydride (EMXDA); 9,9-diethyl-2,3,6,7-xanthenetetracarboxylic dianhydride (EEXDA); etc. Many of the above mentioned dianhydrides (if not all) can also be used in their 'tetra-acid form' (or as mono, di, tri, or tetra esters of the tetra acid), or as their diester acid halides (chlorides). In some embodiments of the present invention however, the dianhydride form is generally preferred because it is generally more reactive than the acid or the ester.

Typically the reaction is conducted in the presence of one or more organic solvents for the dianydride and diamine. Exemplary solvents include N,N-dimethylformamide, N,N-dimethylacetamide, N,N-diethylacetamide, N,N-dimethylmethoxyacetamide, N-methyl-2-pyrrolidone, 1,3-dimethyl-2-imidazolidinone, N-methylcaprolactam, 1,2-dimethoxyethane, bis(2-methoxyethyl) ether, 1,2-bis(2-methoxyethoxy)ethane, bis[2-(2-methoxyethoxy)ethyl] ether, tetrahydrofuran, 1,3-dioxane, 1,4-dioxane, pyridine, picoline, dimethylsulfoxide, dimethylsulfone, tetramethylurea and hexamethylphosphoramide. The reaction temperature is normally between about 15° C. and 75° C., preferably less than about 50° C. The reaction can be carried out under any pressure and ambient pressure is satisfactory. The reaction is typically conducted under any dry inert atmosphere such as nitrogen, helium, and argon. The reaction time depends upon the reactive nature of the reactants, solvent and reaction temperature. The reaction is usually continued for sufficient time to complete formation of a copoly(amic acid oxetane) which is usually from about 0.1 to 50 hours, say, about 2 to 30 hours. The copoly(amic acid oxetane) can be thermally imidized, resulting in the evolution of water, by heating, e.g. at a temperature of at least about 120° C., and often from about 150° C. to 400° C., or chemically imidized.

FOX Diamines

The FOX diamines used in making the copoly(imide oxetane)s of this invention can be represented by the structure

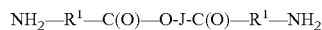

$NH_2-R^1-C(O)-O-J-C(O)-R^1-NH_2$ where J, $R^1$, $R^2$, $R^3$ and m are as defined above.

One source of FOX diamines uses fluorine-containing oxetane oligomers where the oligomers are functionalized to provide the diamine. The functionalization may proceed by any suitable process. A particularly advantageous process is to react hydroxyl-terminated oligomer with an acyl reagent containing a nitro substituent under nucleophilic reaction conditions to provide a di-nitro functionalized oligomer. The di-nitro functionalized oligomer can be readily hydrogenated under hydrogenation conditions, especially mild hydrogenation conditions, to provide the FOX diamine.

The hydroxyl-terminated fluorine containing oxetane oligomers can be represented by the structure:

H—O-J-H where J is as defined above. Examples of the oligomers include, but are not limited to, oligomers made from one or more of 3-(2,2,2-trifluoroethoxymethyl)-3-(2,2,3,3,4,4,4-heptafluorobutoxymethyl)-oxetane, 3-(2,2,2-trifluoroethoxymethyl)-3-(3,3,4,4,5,5,6,6,7,7,8,8,8-trifluorooctyloxymethyl)oxetane, 3-(2,2,3,3,4,4,4-heptafluoro-butoxymethyl)-3-(2,2,3,3,4,4,5,5,6,6,7,7,8,8,8-pentadecafluorooctyloxymethyl)oxetane, 3-(2,2,2-trifluoroethoxymethyl)-3-(3,3,4,4,5,5,6,6,7,7,8,8,9,9,10,10,10-heptadecafluoro-decyloxymethyl)oxetane and 3-(2,2,3,3,4,4,4-heptafluorobutoxymethyl)-3-(3,3,4,4,5,5,6,6,7,7,8,8,9,9,10,10,11,11,12,12,12-heneicosafluorodedecyloxymethyl)oxetane, and block oligomers with diols and hydroxyl-terminated oligomers such as ethylene glycol, propylene glycol, 1,3-propanediol, butanediol, poly(alkylene ethers) including poly(ethylene ether), poly(propylene ether), poly(tetramethylene ether); random or block copolymers of ethylene oxide and propylene oxide including propylene oxide and poly(propylene oxide), random or block copolymers of tetrahydrofuran with minor amounts of a second monomer such as ethylene oxide, propylene oxide, methyl tetrahydrofuran, bis[4-(3-hydroxyphenoxy)phenyl]methane, bis[4-(4-hydroxyphenoxy)phenyl]methane, 1,1-bis[4-(3-hydroxyphenoxy)phenyl]ethane, 1,1-bis[4-(4-hydroxyphenoxy)phenyl]ethane, 1,2-bis[4-(3-hydroxyphenoxy)phenyl]ethane, 1,2-bis[4-(4-hydroxyphenoxy)phenyl]ethane, 2,2-bis[4-(3-hydroxyphenoxy)phenyl]propane, 2,2-bis[4-(4-hydroxyphenoxy)phenyl]propane, 2,2-bis[4-(3-hydroxyphenoxy)phenyl]butane, 2,2-bis[4-(4-hydroxyphenoxy)phenyl]butane, 2,2-bis[4-(3-hydroxyphenoxy)phenyl]-1,1,1,3,3,3-hexafluoropropane, 2,2-bis[4-(4-hydroxyphenoxy)phenyl]-1,1,1,3,3,3-hexafluoropropane, 4,4'-bis(3-hydroyphenoxy)biphenyl, 4,4'-bis(4-hysroxyphenoxy)biphenyl, bis[4-(3-hydroxyphenoxy)phenyl] ketone, bis[4-(4-hydrosyphenoxy)phenyl] ketone, bis[4-(3-hysroxyphenoxy)phenyl] sulfide, bis[4-(4-hydroxyphenoxy)phenyl] sulfide, bis[4-(3-hydroxyphenoxy)phenyl] sulfone and bis[4-(4-hydroxyphenoxy)phenyl] sulfone.

The nucleophilic reaction conditions to convert a hydroxyl-terminated oxetane oligomer to a di-nitro functionalized oligomer can vary widely and optimal conditions will depend upon the acyl reagent used. The acyl reagent is generally present in a stoichiometric excess of that required for the nucleophilic reaction with both hydroxyls of the oligomer, say, a mole ratio of acyl reagent to hydroxyl on the oligomer of between about 1.1:1 to 10:1, and most often between about 1.5:1 to 5:1. Typically the reactions are conducted in the presence of one or more organic solvents for the oligomer and a base. The solvent and the base may be the same or different. Advantageously the base is an organic amine. The base is preferably present in an amount in excess of that required to neutralize the co-product of the nucleophilic reaction. Often the mole ratio of base to acyl reagent is at least about 2:1, and more frequently in the range of about 5:1 to 50:1. The reaction temperature is normally between about 10° C. and 120° C., preferably about 30° C. to 80° C. Preferably the reaction menstruum is under stirring and the acyl reagent is gradually added to avoid undue exotherms. The reaction can be carried out under any pressure and ambient pressure is satisfactory. The reaction is typically conducted under any dry inert atmosphere such as nitrogen, helium, and argon. The reaction time depends upon the reactive nature of the reactants, solvent and reaction temperature. Usually the reaction is complete in about 0.01 to 20 hours.

Exemplary bases that can serve as solvents include trimethylamine, triethylamine, tripropylamine, tributylamine, N,N-dimethylformamide, N,N-dimethylacetamide, N,N-diethylacetamide, N,N-dimethylmethoxyacetamide. Other solvents include ethanol, n-propanol, isobutanol, butanol, hexanol, cyclohexanol, cyclohexane, hexane, benzene, toluene, xylene, methylene chloride, ethylene dichloride, N-methyl-2-pyrrolidone, 1,3-dimethyl-2-imidazolidinone, N-methylcaprolactam, 3-methylphenol, 1,2-dimethoxyethane, bis(2-methoxyethyl) ether, 1,2-bis(2-methoxyethoxy)ethane, bis[2-(2-methoxyethoxy)ethyl] ether, tetrahydrofuran, 1,3-dioxane, 1,4-dioxane, pyridine, picoline, dimethylsulfoxide, dimethylsulfone, tetramethylurea and hexamethylphosphoramide.

The acyl reagent is preferably an acyl halide such as a bromide, chloride or iodide with chlorides being most preferred. Examples of nitro-substituted acyl reagents include, without limitation, 3-nitrobenzaldehyde, 3, nitrobenzoic acid, methyl 3-nitrobnzoate, 3-nitrobenzoyl chloride, 4-nitrobenzoyl chloride, 3-nitrobenzoyl bromide, 4-nitrobenzoyl bromide, 3-nitrobenzoyl iodide, 4-nitrobenzoyl iodide, nitroacetyl bromide, nitroacetyl chloride, nitroacetyl iodide, nitropropionyl chloride, nitrobutyryl chloride, nitrovaleryl chloride, nitrocaproyl chloride, and isomers and lower alkyl and halo-substituted compounds thereof.

The dinitro-functionalized oligomer is then subjected to hydrogenation to convert the nitro groups to amino groups. As the nitro groups are readily hydrogenated to amino groups, mild hydrogenations conditions can be used to prevent undue hydrogenation of other moieties in the oligomer. The hydrogenation is typically conducted in a solvent which may be the same or different from the solvent used in the nitro functionalization of the oligomers. Often, alkanol solvents are preferred. The hydrogenation is conducted in the presence of a catalytically effective amount of hydrogenation catalyst. Hydrogenation catalysts include platinum catalysts, such as, for example, platinum/carbon catalysts (Pt/C) or $PtO_2$; palladium catalysts, such as, for example, Pd/C; rhodium catalysts, such as, for example, Rh/C, $Rh/Al_2O_3$ or $Rh_2O_3$; nickel catalysts, nickel/molybdenum catalysts such as, for example, Raney nickel; or iridium catalysts, and mixtures thereof. Special preference is given to Pd/C or Rh/C. Frequently the reaction menstruum is maintained under mixing such as stirring or agitation when conducted in a batch process. The hydrogenation temperature is usually in the range of about 10° C. to 120° C., preferably about 20° C. to 80° C. Hydrogen is provided at a pressure of between about 100 and 5000 kPa gauge, preferably between about 150 and 1000 kPa gauge. The duration of the reaction in batch mode is generally in the range of about 0.5 to 40 hours. In continuous processes, the reaction menstruum passes through a fixed catalyst bed, often at a liquid hourly space velocity of between about 0.5 and 10 $hr^{-1}$.

EXAMPLES

The following examples are to further illustrate the invention and are not in limitation thereof. All parts and percentages are by mass unless otherwise stated or clear from their context.

Example 1: Synthesis of Dinitro-Terminated Oxetane Oligomer

This example uses a hydroxyl-terminated oxetane available as POLYFOX™ PF-6320, 3-(2,2,2-trifluoroethoxymethyl)-3-(2,2,3,3,4,4,4-heptafluorobutoxymethyl)-oxetane oligomer having an approximate molecular weight of 3400 g/mole. To a glass flask blanketed with nitrogen which contains about 150 milliliters of toluene are charged 60.32 grams of the oligomer. Triethyl amine (14.52 grams) is added and the solution is stirred for about 10 minutes and heated to about 50° C. A previously prepared solution of 10.4 grams of p-nitrobenzoyl chloride dissolved in 150 milliliters of toluene is added to the oligomer-containing solution drop wise over a period of about 30 minutes. The solution is then stirred under reflux for about 16 hours, then cooled to room temperature. The solution is then filtered, washed twice (250 milliliters) with an aqueous solution of 5 mass percent sodium bicarbonate and then once with 250 milliliters of deionized, distilled water. Thereafter the solution is dried over magnesium sulfate. The liquor is then rotary evaporated to yield a viscous, honey-colored oil. The oil is vacuumed dried. The dried sample contains the dinitro-terminated oxetane oligomer.

Example 2: Synthesis of Diamine-Terminated Oxetane Oligomer

A 100 milliliter, mechanically stirred, glass reaction vessel is charged with 8.8 grams of the dinitro-terminated oxetane oligomer of Example 1, 0.445 grams of palladium on carbon hydrogenation catalyst available from Aldrich Chemical Co. having a metal loading of 5 mass percent, and 40 milliliters of anhydrous ethanol. The resulting solution is degassed and subsequently backfilled with hydrogen to 200 kPa gauge. The solution is maintained under agitation for 16 hours. After removing hydrogen, the solution is filtered through diatomaceous earth (CELITE™ available from Celite Corporation, Goleta, Calif., United States) followed by rotary evaporation and vacuum drying. The dried sample contains the diamine of the oxetane oligomer.

Example 3: Synthesis of Copoly(Imide Oxetane)

A series of copoly(imide oxetane)s are prepared using the following general procedure:
1. The diamine-terminated oxetane oligomer is dissolved in N,N-dimethylacetamide to provide an oligomer solution.
2. The other diamine, 4,4'-oxydianiline, is added to a stirred, glass reaction flask and dissolved in N,N-dimethylacetamide.
3. An amount of the oligomer solution is added to the flask to provide a sought mass ratio of the oxetane oligomer to the diamine.
4. The solution in the flask is stirred for about 10 minutes and then dianhydride, 3,3',4,4'-bisphenyltetracarboxylic dianhydride, is added to the flask. The amount of dianhydride added provides a molar ratio of dianhydride to total diamine of about 1.0:0.95. Sufficient N,N-dimethylacetamide is added to provide a 20 mass percent solids solution.
5. The solution is stirred at ambient temperature (about 22° C.) for about 16 hours under an inert gas atmosphere.

The solution contains copoly(amic acid oxetane). Table I summarizes the polymers made.

Example 4: Imidization to Copoly(Imide Oxetane)

Imidization of the polymer material is done using the following general procedure. Samples of each solution made in Example 3 are centrifuged to remove gas bubbles. A film is cast from each sample using a doctor blade to an approximate thickness of about 500 to 750 microns on glass and each film is placed in a forced air drying chamber at room temperature for about 24 to 48 hours to remove solvent and provide a tack-free surface. Some of the films are then thermally imidized under nitrogen using a cure cycle with stages at 150° C., 175° C., 200° C. and 250° C. with a minimum hold of 40 minutes at each stage.

Some of the copoly(amic acid oxetane) solutions are chemically imidized by reaction with acetic anhydride and pyridine. In this procedure, 33.02 grams of a 10 mass percent solids copoly(amic acid oxetane) and N,N-dimethylacetamide solution are poured into a 100 milliliter 3-necked round bottomed flask. Then 3.9 milliliters of pyridine and 3.3 milliliters of acetic anhydride are added to the flask and the reaction mixture is mechanically stirred overnight under an inert atmosphere. After about 16 hours the reaction mixture is poured into a blender containing water resulting in precipitation of the chemically imidized copoly(imide oxetane) product. The copoly(imide oxetane) is filtered, stirred in hot water for several hours, filtered again and allowed to dry.

Example 5: Evaluation of Copoly(Imide Oxetane)

The cast and imidized coatings are evaluated for various characteristics and performance properties.

Modulus of the coatings is determined using a Sintech 2W test frame with a crosshead speed of 5.08 millimeters per minute and analyzed using Testworks 8.0 software (both available from MTS Systems Corporation, Eden Prairie, Minn., United States). See Table I.

A ThermoFisher ESCA lab 250 X-ray photoelectron spectrometer (available from Thermofisher Scientific, Waltham, Mass., United States) is used for XPS analysis.

A FTA 1000B contact angle goniometer available from First Ten Angstroms, Inc., Portsmouth, Va., United States is used to measure the water contact angle with an 8 microliter drop being used. See Table I.

Dust adhesion is evaluated by adhering a 6 millimeter diameter sample of the cast film on the end of a sonication device. The surface is coated with an approximate monolayer of particles having a particle diameter of less than about 30 microns. The sonication device uses a series of sonication steps of increasing magnitude.

With respect to dust adhesion, the copoly(imide oxetane)-containing films exhibit improved surface clearance and potentially lower adhesion values than the homopolymer.

The XPS surface analysis indicates that the fluorine population of the exterior (air-facing) surface of the coating films reaches a plateau at a low fluorine-containing oxetane moiety content in the copoly(imide oxetane) material. The data are presented in Table I. For sake of comparison, the fluorine atomic concentration of the oxetane oligomer is about 29 atomic percent. The interior surface (glass-facing surface) has a fluorine population higher than that of the bulk, but less than that of the exterior surface (air-facing surface) which is also reported in Table I. The XPS analysis thus confirms an unexpected migration of the fluorine-containing oxetane moieties in the copoly(imide oxetane) to the surface, and further indicates that only a very small amount of the oxetane oligomer is required to provide sought low surface energies. Although the presence of the oxetane oligomer does not unduly adversely affect the mechanical properties of the copoly(imide oxetane) at somewhat higher levels, the ability to achieve the low surface energies with very small amounts of the oxetane oligomer would not detract from the desirable bulk properties of the copoly(imide oxetane) material.

TABLE I

| Diamine oxetane oligomer, mass % | Modulus, MPa | Break Stress, MPa | Elongation at Break, % | Water Contact Angle, ° | Exterior Surface Fluorine, Atomic % | Glass Surface Fluorine, Atomic % |
|---|---|---|---|---|---|---|
| 0 | 3590 | 141 | 10.1 | 81 | 5 | 2 |
| 0.01 | 3560 | 142 | 8.3 | 93 | | |
| 0.1 | 3570 | 142 | 9.2 | 95 | 14 | 5 |
| 0.2 | 3510 | 139 | 11.5 | 95 | 14 | |
| 0.4 | 3450 | 138 | 7.5 | 94 | 20 | |
| 0.5 | 3350 | 142 | 5.5 | 94 | 16 | 9 |
| 0.8 | 3460 | 138 | 11.2 | 94 | 17 | |
| 1.0 | 3440 | 141 | 8.7 | 98 | 19 | 8 |
| 2.0 | 3380 | 138 | 8.7 | 94 | 17 | |
| 5.0 | 3140 | 126 | 9.7 | 95 | 18 | 4 |

What is claimed:

1. A copoly(imide oxetane) having the structure represented by:

-(G-M)-(D-M)- wherein:

G is represented by the formula

=N—R$^1$—C(O)—O-J-C(O)—R$^1$—N= wherein:

J is [CH$_2$—CR$^2$R$^3$—CH$_2$—O]$_m$ or [(CH$_2$—CR$^2$R$^3$—CH$_2$—O)$_p$—(R$^6$—O)$_q$—(CH$_2$—CR$^2$R$^3$—CH$_2$—O)$_r$] wherein R$^6$ is substituted or unsubstituted aliphatic or aromatic moiety of 2 to 16 carbons;

R$^1$ is aliphatic or aromatic hydrocarbon moiety of 1 to 10 carbon atoms;

R$^2$ is —H, —F, or alkyl of 1 to 6 carbon atoms;

R$^3$ is —F, —R$^4$H$_{(n-a)}$F$_a$, —R$^5$—O—R$^4$H$_{(n-a)}$F$_a$, and —O—R$^4$H$_{(n-a)}$F$_a$, wherein R$^4$ is an alkyl or ether moiety of 1 to 30 carbons, R$^5$ is an alkyl moiety of 1 to 30 carbons, a is an integer of 3 to n, and n is twice the number of carbon atoms in the alkyl moiety plus 1; and m is between about 4 and 500, p is between about 4 and 150, q is between about 1 and 150, and r is an integer;

M is represented by the formula (—C(O))$_2$-L-(C(O)—)$_2$ wherein:

L is a hydrocarbyl-containing moiety of 2 to 100 carbon atoms optionally containing divalent radicals selected from the group consisting of oxygen, silyl, sulfur, carbonyl, sulfonyl, phosphonyl, perfluoro, tertiary amino, and imido;

D is represented by the formula

=N—Z—N= wherein:

Z is a hydrocarbyl-containing moiety of 1 to 100 carbon atoms optionally containing divalent radicals selected from the group consisting of oxygen, sulfur, silyl, carbonyl, sulfonyl, phosphonyl, perfluoro, tertiary amino, and imido.

2. The copoly(imide oxetane) of claim 1 wherein the omega carbon of R$^4$ has three fluoride substituents and wherein m is between 6 and 100.

3. The copoly(imide oxetane) of claim 2 containing 0.002 to 15 mass percent of G.

4. The copoly(imide oxetane) of claim 3 which is a block co-polymer.

5. The copoly(imide oxetane) of claim 3 which is a random co-polymer.

6. A coating having an outer surface and a bonding surface comprising the copoly(imide oxetane) of claim 1, said coating having an anisotropic distribution of fluorine atoms over its thickness with a higher concentration at the outer surface.

7. The coating of claim 6 having a water contact angle of at least 90° at the outer surface.

8. A method for coating a substrate with the copoly(imide oxetane) of claim 1, the method comprising applying on the substrate a solution containing a copoly(amic acid oxetane) having the structure represented by:

-(G-A)-(D-A)- wherein:

G is represented by the formula

—NH—R$^1$—C(O)—O-J-C(O)—R$^1$—HN— wherein:

J is [CH$_2$—CR$^2$R$^3$—CH$_2$—O]$_m$ or [(CH$_2$—CR$^2$R$^3$—CH$_2$—O)$_p$—(R$^6$—O)$_q$—(CH$_2$—CR$^2$R$^3$—CH$_2$—O)$_r$] wherein R$^6$ is substituted or unsubstituted aliphatic or aromatic moiety of 2 to 16 carbons;

R$^1$ is aliphatic or aromatic hydrocarbon moiety of 1 to 10 carbon atoms;

R$^2$ is —H, —F, or alkyl of 1 to 6 carbon atoms;

R$^3$ is —F, —R$^4$H$_{(n-a)}$F$_a$, —R$^5$—O—R$^4$H$_{(n-a)}$F$_a$, and —O—R$^4$H$_{(n-a)}$F$_a$, wherein R$^4$ is an alkyl or ether moiety of 1 to 30 carbons, R$^5$ is an alkyl moiety of 1 to 30 carbons, a is an integer of 3 to n, and n is twice the number of carbon atoms in the alkyl moiety plus 1; and m is between about 4 and 500, p is between about 4 and 150, q is between about 1 and 150, and r is an integer;

A is represented by the formula

—[C(O)    C(O)]—
      >L<
HOC(O)    (O)COH wherein:

L is a hydrocarbyl-containing moiety of 2 to 100 carbon atoms optionally containing divalent radicals selected from the group consisting of oxygen, silyl, sulfur, carbonyl, sulfonyl, phosphonyl, perfluoro, tertiary amino, and imido;

D is represented by the formula

—NH—Z—NH— wherein:
Z is a hydrocarbyl-containing moiety of 1 to 100 carbon atoms optionally containing divalent radicals selected from the group consisting of oxygen, sulfur, silyl, carbonyl, sulfonyl, phosphonyl, perfluoro, tertiary amino, and imido;

in a volatile solvent to form a copoly(amic acid oxetane) coating, and subjecting the copoly(amic acid oxetane) coating to drying and imidization conditions to form the anisotropic copoly(imide oxetane) coating.

9. A polymer composite comprising a copolymer containing the copoly(imide oxetane) of claim 1 and a particulate filler, wherein the polymer composite has a water contact angle of at least 100°.

10. An article of manufacture comprising a polymeric matrix and the copoly(imide oxetane) of claim 1, said article having an outer surface, and said article of manufacture having a higher concentration of fluorine atoms at the outer surface than that of the polymeric matrix without the copoly (imide oxetane).

11. The article of manufacture of claim 10 which is a cast article of manufacture.

12. The article of manufacture of claim 10 which is a molded article of manufacture.

13. A method for making the article of manufacture of claim 10 comprising W forming the polymeric matrix containing comprising a copoly(amic acid oxetane) having the structure represented by:

-(G-A)-(D-A)- wherein:
G is represented by the formula

—NH—R$^1$—C(O)—O-J-C(O)—R$^1$—HN— wherein:
J is [CH$_2$—CR$^2$R$^3$—CH$_2$—O]$_m$ or [(CH$_2$—CR$^2$R$^3$—CH$_2$—O)$_p$—(R$^6$—O)$_q$—(CH$_2$—CR$^2$R$^3$—CH$_2$—O)$_r$] wherein R$^6$ is substituted or unsubstituted aliphatic or aromatic moiety of 2 to 16 carbons;

R$^1$ is aliphatic or aromatic hydrocarbon moiety of 1 to 10 carbon atoms;

R$^2$ is —H, —F, or alkyl of 1 to 6 carbon atoms;

R$^3$ is —F, —R$^4$H$_{(n-a)}$F$_a$, —R$^5$—O—R$^4$H$_{(n-a)}$F$_a$, and —O—R$^4$H$_{(n-a)}$F$_a$, wherein R$^4$ is an alkyl or ether moiety of 1 to 30 carbons, R$^5$ is an alkyl moiety of 1 to 30 carbons, a is an integer of 3 to n, and n is twice the number of carbon atoms in the alkyl moiety plus 1; and m is between about 4 and 500, p is between about 4 and 150, q is between about 1 and 150, and r is an integer;

A is represented by the formula

—[C(O)  C(O)]—
>L<
HOC(O)  (O)COH wherein:
L is a hydrocarbyl-containing moiety of 2 to 100 carbon atoms optionally containing divalent radicals selected from the group consisting of oxygen, silyl, sulfur, carbonyl, sulfonyl, phosphonyl, perfluoro, tertiary amino, and imido;

D is represented by the formula

—NH—Z—NH— wherein:
Z is a hydrocarbyl-containing moiety of 1 to 100 carbon atoms optionally containing divalent radicals selected from the group consisting of oxygen, sulfur, silyl, carbonyl, sulfonyl, phosphonyl, perfluoro, tertiary amino, and imido;

into a first article having an outer surface and (2) subjecting the first article to imidization conditions to form the article of manufacture comprising the copoly(imide oxetane).

14. The method of claim 13 wherein the article of manufacture is a cast article of manufacture.

15. The method of claim 13 wherein the article of manufacture is a molded article.

16. The method of claim 15 wherein the molded article is produced from dry polymeric matrix particles comprising the copoly(amic acid oxetane) and formed into the shape of the article under pressure and imidization conditions.

17. A method for making the article of manufacture of claim 10 comprising (1) forming a polymeric matrix comprising a copoly(amic acid oxetane) into a first article having an outer surface, (2) contacting the outer surface with at least one of
(i) at least one diamine oligomer represented by the formula:

(E)$_y$R$^1$—C(O)—O-J-C(O)—R$^1$(E)$_y$ wherein:
J is [CH$_2$—CR$^2$R$^3$—CH$_2$—O]$_m$ or [(CH$_2$—CR$^2$R$^3$—CH$_2$—O)$_p$—(R$^6$—O)$_q$—(CH$_2$—CR$^2$R$^3$—CH$_2$—O)$_r$] wherein R$^6$ is substituted or unsubstituted aliphatic or aromatic moiety of 2 to 16 carbons;

E is —NH$_2$;

y is 1 or 2;

R$^1$ is aliphatic or aromatic hydrocarbon moiety of 1 to 10 carbon atoms;

R$^2$ is —H, —F, or alkyl of 1 to 6 carbon atoms;

R$^3$ is —F, —R$^4$H$_{(n-a)}$F$_a$, —R$^5$—O—R$^4$H$_{(n-a)}$F$_a$, and —O—R$^4$H$_{(n-a)}$F$_a$, wherein R$^4$ is an alkyl or ether moiety of 1 to 30 carbons and the omega carbon of R$^4$ has three fluoride substituents, R$^5$ is an alkyl moiety of 1 to 30 carbons, a is an integer of 3 to n, and n is twice the number of carbon atoms in the alkyl moiety plus 1; and m is between about 6 and 100, p is between about 4 and 150, q is between about 1 and 150, and r is an integer, and (ii) at least one copoly(amic acid oxetane) having the structure represented by:

-(G-A)-(D-A)- wherein:
G is represented by the formula

—NH—R$^1$—C(O)—O-J-C(O)—R$^1$—HN— wherein:

J is $[CH_2-CR^2R^3-CH_2-O]_m$ or $[(CH_2-CR^2R^3-CH_2-O)_p-(R^6-O)_q-(CH_2-CR^2R^3-CH_2-O)_r]$ wherein $R^6$ is substituted or unsubstituted aliphatic or aromatic moiety of 2 to 16 carbons;

$R^1$ is aliphatic or aromatic hydrocarbon moiety of 1 to 10 carbon atoms;

$R^2$ is —H, —F, or alkyl of 1 to 6 carbon atoms;

$R^3$ is —F, $-R^4H_{(n-a)}F_a$, $-R^5-O-R^4H_{(n-a)}F_a$, and $-O-R^4H_{(n-a)}F_a$, wherein $R^4$ is an alkyl or ether moiety of 1 to 30 carbons, $R^5$ is an alkyl moiety of 1 to 30 carbons, a is an integer of 3 to n, and n is twice the number of carbon atoms in the alkyl moiety plus 1; and m is between about 4 and 500, p is between about 4 and 150, q is between about 1 and 150, and r is an integer;

A is represented by the formula

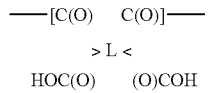

wherein:

L is a hydrocarbyl-containing moiety of 2 to 100 carbon atoms optionally containing divalent radicals selected from the group consisting of oxygen, silyl, sulfur, carbonyl, sulfonyl, phosphonyl, perfluoro, tertiary amino, and imido;

D is represented by the formula

—NH—Z—NH— wherein:

Z is a hydrocarbyl-containing moiety of 1 to 100 carbon atoms optionally containing divalent radicals selected from the group consisting of oxygen, sulfur, silyl, carbonyl, sulfonyl, phosphonyl, perfluoro, tertiary amino, and imido, to produce a second article, and (3) subjecting the second article to imidization conditions to form the article of manufacture comprising the poly(imide oxetane).

* * * * *